United States Patent [19]
Majocha et al.

[11] Patent Number: 5,231,000
[45] Date of Patent: Jul. 27, 1993

[54] ANTIBODIES TO A4 AMYLOID PEPTIDE

[75] Inventors: Ron Majocha, Wayland; Charles A. Marotta, Cambridge, both of Mass.; Sayeeda Zain, Pittsford, N.Y.

[73] Assignees: The McLean Hospital, Belmont, Mass.; University of Rochester, Rochester, N.Y.

[21] Appl. No.: 733,375

[22] Filed: Jul. 22, 1991

Related U.S. Application Data

[63] Continuation of Ser. No. 105,751, Oct. 8, 1987.

[51] Int. Cl.$^5$ .................. G01N 33/53; G01N 33/564; G01N 33/577; C12N 5/20
[52] U.S. Cl. ...................... 435/7.1; 435/7.2; 435/7.21; 435/240.27; 530/388.1; 436/501; 436/506
[58] Field of Search ................ 530/387; 435/240.27, 435/7.1, 960, 7.2, 388.2; 436/518, 529–530, 548, 512, 501, 507; 424/85.8

[56] References Cited

U.S. PATENT DOCUMENTS 4,376,110 3/1983 David et al. .
4,666,829 5/1987 Glenner .

OTHER PUBLICATIONS

Pardridge, W. M. et al May 1987 Biochem Biophys Res. Comm 145(1):241-8 "High Molecular . . . ".
Wong, C. W. et al. Dec. 1985, P.N.A.S. 82; 8729–8732, "Neuritic plaques . . . ".
Kang, J. et al. Feb. 1987 Nature 325:733-736 "The Precursor of Alzheimer's Diseases Amyloid . . . ".
Kohler, G and C. Milstein, Nature (256:495-8), Aug. 1975, "Continuous cultures . . . ".
White et al., *Principles of Biochemistry*, Fourth Edition, McGraw-Hill, pp. 92–93 (1968).
Salim et al., *Familial Alzheimer's Disease: Molecular Genetics, Clinical Prospects and Societal Issues*, Marcel Dekker, N.Y., pp. 153–165 (1989).
Sajdel-Sulkowska et al., *JAGS* 36:558–564 (1988).
Majocha et al., *Proc. Natl. Acad. Sci., U.S.A.*, 85:6182–6186 (1988).
Benes, F. M. et al., *Soc. Neurosci.* 13:abs. 316.15, p. 1153 (1987).
Glenner, G. G., et al., *Biochem. Biophys. Res. Comm.* 120:885–890 (1984).
Glenner, G. G., et al., *Biochem. Biophys. Res. Comm.* 122:1131–1135 (1984).
Masters, C. L., et al., *Proc. Natl. Acad. Sci. USA* 82:4245–4249 (1985).
Masters, C. L., et al., *EMBO. J.* 4:2757–2763 (1985).
A copy of International Search Report of the International Patent Application No. PCT/US88/03590.
Pardridge et al., *Biochem. Biophys. Res. Comm.* 145:241–248 (1987).
Robakis et al., *Chemical Abstr.* 107: Abstr. No. 71938a (1987).

*Primary Examiner*—Christine M. Nucker
*Assistant Examiner*—T. Cunningham
*Attorney, Agent, or Firm*—Sterne, Kessler, Goldstein & Fox

[57] ABSTRACT

Monoclonal antibodies to a 28-mer peptide present within A4-amyloid are described. These antibodies exhibit unexpected specificity for amyloid plaque structures previously unrecognized in Alzheimer's disease brains. These monoclonal antibodies are useful as reagents for use in assays and imaging of A4-amyloid in Alzheimer's disease patients.

9 Claims, 1 Drawing Sheet

Figure 1.

β-polypeptide:  N-asp-ala-glu-phe-arg-his-asp-ser-gly-tyr-
                   1
gln-val-his-his-gln-lys-leu-val-phe-phe-ala-glu-asp-val-C
 11                                                    24

A4:  N-asp-ala-glu-phe-arg-his-asp-ser-gly-tyr-glu-val-his-
        1                                      11
his-gln-lys-leu-val-phe-phe-ala-glu-asp-val-gly-ser-ser-ala-C
                                            27  28

USP:  N-asp-ala-glu-phe-arg-his-asp-ser-gly-tyr-gln-val-his-
         1                                      11
his-gln-lys-leu-val-phe-phe-ala-glu-asp-val-gly-ser-asn-lys-C
                                            27  28

ANTIBODIES TO A4 AMYLOID PEPTIDE

BACKGROUND OF THE INVENTION

The present invention was made utilizing funds of the United States Government. The United States Government is hereby granted a worldwide royalty fee, paid up, non-exclusive license to the invention.

This application is a continuation of application Ser. No. 07/105,751, filed Oct. 8, 1987.

FIELD OF THE INVENTION

The present invention relates to antibodies with specificity to A4 amyloid polypeptide found in the brain of Alzheimer's Disease (AD) patients, and to uses thereof, especially for the neuropathological definition of AD senile plaque subtypes, and for the fine, detailed imaging of AD brain tissue.

BRIEF DESCRIPTION OF THE BACKGROUND ART

Although the presence of amyloid in the plaques of Alzheimer's Disease patients was noted over 60 years ago (Divry, 1927), molecular mechanisms that produce amyloid in the aged human brain and for the increased deposition of this fibrous material in Alzheimer's Disease remain unknown. Also undescribed is the contribution, if any, of amyloid to the active process of plaque formation vis-a-vis a secondary and more passive role that indicates only the terminal stages of parenchymal deterioration.

Recently, some progress has been made in defining the partial structure of amyloid fibrillary protein. Glenner et al. (1984a) purified amyloid from meningeal vessels of an AD brain; a 4.2 kD polypeptide was isolated and shown to have a unique 24 amino acid sequence ($\beta$-polypeptide, FIG. 1). A polypeptide of similar sequence was subsequently isolated from the cerebrovascular amyloid of a Down's syndrome brain (Glenner et al., 1984b); a single amino acid substitution, of glutamic acid for glutamine at position 11, distinguished the two polypeptides. Similar results were independently obtained by Masters et al. (1985a) who partly purified and analyzed amyloid plaque cores from the AD cerebral cortex; the 28 amino acid sequence of the Glu variant was obtained (A4 sequence, FIG. 1). The A4 sequence differs from the $\beta$-polypeptide disclosed by Glenner et al. (U.S. Pat. No. 4,666,829) by the three amino acids at positions 11, 27 and 28. The significance of this report is that the A4 was derived from amyloid plaque cores, a hallmark feature of AD. The amino acid sequence of A4 varies from that of the $\beta$-polypeptide derived from vascular amyloid (see FIG. 1).

Using polyclonal antisera to a synthetic $\beta$-amyloid polypeptide containing residues 1 through 10 (FIG. 1), it was shown that neuritic plaque amyloid shares antigenic determinants with the similar fibrillary lesion of cerebral vessels (Wong et al., 1985). The same antisera failed to detect neurofibrillary tangles (NFTs). By contrast, antiserum raised against residues 1 to 11 of the A4 polypeptide failed to detect vascular amyloid or neuritic plaques but, rather, exhibited exclusive specificity for the NFT; and antisera to the A4 peptide extending from residues 11 to 23 stained both plaques and vessels (Masters et al., 1985b). Thus, there is precedent to believe that antibodies to the $\eta$-peptide and the A4 peptide are not identical with regard to their specificities.

Glenner et al., U.S. Pat. No. 4,666,829 disclose the preparation of antibodies using the first 10 amino acids of the $\beta$-amyloid polypeptide (FIG. 1).

SUMMARY OF THE INVENTION

In order to facilitate studies on the molecular mechanisms involved in fibrous protein accumulation in the aged AD demented brain and to provide improved neuropathological aids for the diagnosis of AD subtypes, we prepared antibodies, both polyclonal and monoclonal antibodies (Mabs), to a synthetic amyloid polypeptide with the known 28 amino acid A4 sequence (Masters et al., 1985a, FIG. 1). The Mabs were routinely characterized on AD cortical and hippocampal sections, and shown to be useful to carry out an analysis of individual epitopic sites of Alzheimer—type amyloid.

Three Mabs were specifically and extensively characterized and used to obtain information on the following: (a) detailed morphological features of plaque amyloid revealed by individual target epitopes; (b) the identification of new subtypes of amyloid deposits in the AD brain; (c) the relationship of plaque maturation to the deposition of epitopes. The latter study was made possible through computer-assisted imaging and microdensitometry.

The antibodies can be used in in vitro immunoassay procedures for AD-amyloid. They can also be used in imaging (e.g. cytochemical or in vivo) neurons for evidence of AD-amyloid. For immunoassays and/or imaging, the antibodies can be detectably labelled with, e.g., radio, enzyme or fluorescent labels. They can also be immobilized on insoluble carriers.

The striking aspect of Mabs prepared to the A4 28-mer peptide is that they define previously undescribed amyloid formations in the AD brain. These Mabs represent, therefore, a unique class of Mabs.

BRIEF DESCRIPTION OF THE FIGURES

FIG. 1 shows the amino acid sequence of the $\beta$-polypeptide (Glenner et al., 1984 a,b), the synthetic amyloid A4 peptide (Masters et al., 1985a) used as the antigen in the present invention, and the polypeptide disclosed by Glenner et al. (U.S. Pat. No. 4,666,829 (1987). The difference between the A4 polypeptide and the other two polypeptides are depicted by underlining (amino acids 11, 27 and 28).

DESCRIPTION OF THE PREFERRED EMBODIMENTS

The antibodies of the present invention have specificity to one or more epitopes present on the A4 28-mer peptide shown in FIG. 1. The antibodies of the invention can be polyclonal or monoclonal, provided that they are made with the A4 28-mer polypeptide as an immunogen. Both of these types of antibodies can be utilized in the multiple applications described herein below.

The term "epitope" as used in this invention is meant to include any determinant responsible for specific interaction with an antibody molecule. Epitopic determinants usually consist of chemically active surface groupings of molecules such as amino acids or sugar side chains and have specific three dimensional structural characteristics as well as specific charge characteristics.

Polyclonal antibodies can be generated in any suitable animal such as, for example, mice, rabbits or goats. The A4-amyloid 28-peptide can be injected by itself or linked to appropriate immunoactivating carriers, such as KLH. Further detailed descriptions of immunization protocols can be found in the Examples.

Monoclonal antibodies can be produced in various ways using techniques well understood by those having ordinary skill in the art and will not be repeated here. Details of these techniques are described in such books as *Monoclonal Antibodies-Hybridomas: A New Dimension in Biological Analysis,* edited by Roger H. Kennett et al., published by Plenum Press (1980).

For example, additional hybridomas to those specifically disclosed in the invention, which produce monoclonal antibodies which enable the detection of A4-amyloid can be easily produced and isolated with minimal screening.

Hybridomas producing monoclonal antibodies specific for epitopes which are found on the A4 28-mer peptide are most effectively produced by first immunizing an animal from which hybridomas can be produced such as, for example, a Balb/c mouse, with initial subcutaneous injections of the 28-mer peptide in Freund's adjuvant, followed by booster injections within a few days. The fusion can be carried out using any of the techniques commonly known to those of ordinary skill in the art. The screening of the hybridomas to determine which ones are producing monoclonal antibodies specific for the 28-mer peptide is straightforward and can be done either in a standard ELISA or RIA format. For example, in an RIA screening format the culture supernatant, or ascites fluid from a hybridoma producing monoclonal antibody is reacted with $^{125}$I-28-mer peptide.

The antibodies of the present invention can be utilized in immunoassays for the detection of A4-amyloid polypeptide wherever it may occur, including fluid or semi-fluid human samples. The immunoassays can be competitive or sandwich, as is otherwise well known they all depend on the formation of antibody-antigen immune complex. These assays are not described herein in any further detail, as they are well known to those of skill in the art.

For purposes of the assays, the antibodies can be immobilized or labeled.

There are many carriers to which the antibodies can be bound for immobilization and which can be used in the present invention. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the antibodies, or will be able to ascertain such, using routine experimentation.

Depending on the particular embodiment of the invention, one or more of the antibodies will be coupled with a detectable label such as an enzyme, radioactive isotope, fluorescent compound, chemiluminescent compound, or bioluminescent compound.

Those of ordinary skill in the art will know of other suitable labels for binding to the antibodies or will be able to ascertain such using routine experimentation. Furthermore, the binding of these labels to the antibodies can be done using standard techniques commonly known to those of ordinary skill in the art.

The antibodies can be bound to an enzyme. This enzyme, in turn, when later exposed to its substrate will react to the substrate in such a manner as to produce a chemical moiety which can be detected, as, for example, spectrophotometric or fluorometric means. Examples of enzymes that can be used to detectably label are malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of an antibody can also be detected by labeling it with a radioactive isotope. The presence of the radioactive isotope could then be determined by such means as the use of a gamma counter or a scintillation counter. Isotopes which are particularly useful are $^3$H, $^{125}$I, $^{32}$P, $^{35}$S, $^{14}$C, $^{51}$Cr, $^{36}$Cl, $^{57}$Co, $^{58}$Co, $^{59}$Fe, $^{75}$Se, and $^{152}$Eu.

It is also possible to detect the presence of the antibody by labeling it with a fluorescent compound. When the fluorescently labeled antibody is exposed to light of the proper wavelength, its presence can then be detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

Another way in which the antibody can be detectably labeled is by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, aromatic-acridinium ester, imidazole, acridinium salt, and oxalate ester.

Likewise, a bioluminescent compound may also be used to label the antibody. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably-labeled third antibody in lyophilized form or in solution. Such a kit can be used for sandwich assays. See, e.g., David et al. U.S. Pat. No. 4,376,110 herein incorporated by reference.

In addition, the carrier means may also contain a plurality of containers each of which comprises different, predetermined amounts of known A4-amyloid antigen. These latter containers can then be used to prepare a standard curve into which can be interpolated the results obtained from the sample containing the unknown amount of A4-amyloid antigen.

Imaging can be carried out in vitro or in vivo. In vitro imaging can be done with the labels mentioned previously. In vivo imaging is done with diagnostically effective labeled antibodies. The term "diagnostically effective" means that the amount of detectably labeled antibody administered is sufficient to enable detection of the site of amyloid presence when compared to a background signal.

Generally, the dosage of detectably labeled antibody for diagnosis will vary depending on considerations such as age, condition, sex, and extent of disease in the patient, counterindications, if any, and other variables, to be adjusted by the individual physician. Dosage can vary from 0.01 mg/kg to 2,000 mg/kg, preferably 0.1 mg/kg to 1,000 mg/kg.

The term "diagnostically labeled" means that the immunoglobulin has attached to it a diagnostically detectable label.

There are many different imaging labels and methods of labeling known to those of ordinary skill in the art. Examples of the types of labels which can be used in the present invention include radioactive isotopes and paramagnetic isotopes.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140-200 keV range, which may be readily detected by conventional gamma cameras.

For in vivo diagnosis, radionuclides may be bound to antibody either directly or indirectly by using an intermediary functional group. Intermediary functional groups which are often used to bind radioisotopes which exist as metallic ions to antibody are diethylenetriaminepentaacetic acid (DTPA) and ethylenediaminetetracetic acid (EDTA). Typical examples of metallic ions which can be bound to immunoglobulins are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

The antibodies used in the method of the invention can also be labeled with paramagnetic isotopes for purposes of in vivo diagnosis. Elements which are particularly useful (as in Magnetic Resonance Imaging (MRI) techniques) in this manner include $^{157}Gd$, $^{55}Mn$, $^{162}Dy$, $^{52}Cr$, and $^{56}Fe$.

Preparations of the imaging antibodies for parenteral administration include sterile aqueous or nonaqueous solutions, suspensions, and emulsions. Examples of nonaqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*. 16th ed., Mac Eds, 1980.

EXPERIMENTAL

MATERIALS AND METHODS

Postmortem Brain Tissues

All formalin-fixed postmortem brains were obtained from the McLean Hospital Brain Tissue Resource Center. Prefrontal cortex (PC) or hippocampal sections were used.

Preparation and Characterization of the Synthetic Amyloid Polypeptide

The A4 amyloid polypeptide of 28 residues (FIG. 1), corresponding to the previously reported sequence of Masters et al. (1985a), was synthesized on a Biosearch SAM2 synthesizer using the general procedure of Merrifield (1963). Purification was achieved with a 3 X 65 cm column of Sephadex G50 (10–40 $\mu$). Aliquots were removed, spotted onto TLC plates and sprayed with fluorescamine to locate protein. Material was pooled and loaded onto an analytical HPLC column (Vydac $C_{18}$, catalog No. 218TP54). Elution was carried out at a flow rate of 1.7 ml/min. with 0.05% trifluoroacetic acid/$H_2O$ for 5 min followed by a 5–100% linear gradient of 0.05% $TFA/CH_3CH$ for 17 min. The optical density profile at 230 nm revealed a single major peak that was further analyzed. Amino acid analysis was carried out in 6M HCl containing 1% phenol for 18 hours at 110° C. The sample was dried under $N_2$, dissolved in citrate buffer and analyzed with an LKB 4151 Alpha Plus amino acid analyzer. Amino acid analyses were consistent with the published sequence and indicated an approximate yield of 95–98%. Peptide samples were stored as a dry powder at −20° C. until used. For some experiments, the peptide was linked to Kehole Limpet Hemocyamin (BABCO, Berkeley, Calif.) prior to use.

Preparation of Polyclonal Antibodies (Pabs)

New Zealand white female rabbits were used for the production of polyclonal antibodies to the synthetic amyloid peptide. In some cases the 28-mer A4-amyloid polypeptide (AP) as shown in FIG. 1 linked to KLH was used as the antigen. Subdermal injection was carried out using 1 mg of AP that had been emulsified in Freund's complete adjuvant. After 3 weeks the animals were bled and tested for reactivity. Animals were injected again after 3 weeks using 1 mg of AP in Freund's incomplete adjuvant. Two weeks later the serum was tested and was observed to give a positive reaction at 1/1,000 dilution. Rabbits were then injected with 1 mg AP for 2 monthly intervals after which the serum was positive at a dilution of greater than 1/10,000 when assayed by immunoblotting.

Preparation of Monoclonal Antibodies (Mabs)

Balb/c mice were injected subdermally with 1 mg each of AP in Freund's complete adjuvant. After 3 weeks sera were positive at a dilution of 1/1,000 using the assays described. At 5 and 4 days prior to fusion 100 $\mu$g of AP was injected both subcutaneously and intraperitoneally in phosphate buffered saline. Spleen cells were isolated and fused with plasmacytoma P3 NS1/1-4 Ag-1 cells (Galfre et al., 1977). Supernatants were tested for antibody activity after 10–14 days using the assay procedures described below. Positive colonies were subcloned by limiting dilution and used in further experimentation. One hybridoma, designated 10H3, has been deposited before the filing date of the present application at the American Type Culture Collection, Rockville, Md., under the terms of the Budapest Treaty and given accession number HB9542.

Dot Blot Assay

Antibodies were tested for reactivity to AP using the BioRad dot blot apparatus according to the manufacturer's directions. For initial screening, 1 mg of AP was sonicated in 0.5 ml of 1% sodium dodecylsulfate in $H_2O$ and added to an equal volume of 2.5% Triton X-100, 0.3M NaCl, 40 mM Tris HCl, pH 7.4. One $\mu g$ AP was added to each well followed by 50 $\mu l$ of 10% BSA. For Mab assays, 150 $\mu l$ of culture supernatant was added per well. Pab assays used serum diluted 1/500, 1/1,000 and 1/10,000 in 150 $\mu l$ Tris buffered saline (TBS) containing 0.15M sodium chloride, 20 mM Tris, pH 7.4. After filtration TBS was used for intermediate washes between antibody additions and prior to adding substrate. 50 $\mu l$ of horseradish peroxidase-conjugated affinity purified, goat anti-mouse or anti-rabbit IgC (Cappel), diluted 1/2,000 in 5% BSA, 0.5% Triton X-100, 0.15M NaCl, 20 mM Tris hydrochloride, pH 7.4 was added to each well. The reaction product was visualized using diaminobenzidine, 0.5 mg/ml, imidazole, mg/ml, and $H_2O_2$, 0.015%. Negative controls consisted of tissue culture media or pre-immune sera, omission of AP, and addition of a monoclonal antibody supernatant specific for a protein other than AP. For subsequent assays, the amount of antigen per well was varied over the range 0.001-1 $\mu g$ and antibodies were tested at different dilutions. For these assays, individual strips of nitrocellulose containing various amounts of antigen were immunostained as described by Brown et al. (1983).

PAGE Procedures

PAGE procedures were carried out as described previously (Brown et al., 1981, 1982). Variations from the published procedures are described in the text.

Immunoblot Assay

Electrophoretic transfer of proteins to nitrocellulose membranes and immunostaining procedures were carried out as previously described (Brown et al., 1983).

Immunohistology

Formalin fixed human postmortem brain tissue was cut on a vibrotome at 50 $\mu m$. All sectioned material were pre-treated prior to staining for 10 min by incubation in 1% $H_2O_2$. The reaction was stopped after 7 min. by placing the sections in water. Tissues were mounted on gelatinized glass slides, air dried and coverslipped using Permount (Fisher). Immune serum was applied at a dilution of 1/1000, pre-immune serum at a dilution of 1/200 and Mab culture supernatants were undiluted.

Thioflavin S Staining

Formalin-fixed sections were placed in a 0.1% solution of Thioflavin S (Sigma) in TBS for 10 min. Excess stain was removed by placing the tissue sections in 70% ethanol for to 2 min and then in water. Sections were coverslipped using a solution containing 20% polyvinyl alcohol (Sigma), 10% glycerol and 50 mM Tris HCl, pH 8.5. Where indicated in the text, double staining was carried out on the same tissue: a section stained with Thioflavin S was subsequently stained by means of the immunocytochemical procedure described above.

Computer-Assisted Image Enhancement

Specimens of prefrontal cortex immunostained for amyloid protein were visualized through a Leitz Laborlux 12 light microscope equipped with a MCI 65 televideo camera that interfaced with a computer. The transmitted images of immunostained amyloid deposits were processed by the computer using software equipped with pseudocolor optical density coding. The transmitted image was reconstructed on a separate monitor according to the individual colors assigned to each level of gray in the image. Thus, internal density variations within amyloid deposits could be assessed.

RESULTS

Peptide Preparation and Characterization

A synthetic amyloid peptide (AP) of 28 amino acids (FIG. 1), with a calculated molecular weight of 3.2 kD, was synthesized and then analyzed by PAGE procedures prior to immunological studies. The AP was dissolved in PAGE sample buffer containing 2% SDS, 5% mercaptoethanol, and 9.5 M urea and was electrophoresed on a 10% gel containing 0.1% SDS. After staining with Coomassie blue the peptide appeared as a broad band at approximately 23-25 kD and a narrow band that migrated at the gel front during electrophoresis. The higher molecular weight species appeared to be an aggregate since it was eliminated by adding urea to the separating gel: the AP was dissolved in sample buffer containing 9.5M urea and electrophoresed on a 10% or 15% gel that contained 6M urea and 2% SDS. After staining with Coomassie blue, the predominant species appeared as a 3-4 kD band which is consistent with the mass of a denatured polypeptide. Thus, the synthetic AP has aggregational properties not unlike the naturally occurring amyloid protein of 4 kD (Masters et al., 1985b). In experiments that follow, antibodies to AP were characterized with respect to both the aggregated and denatured forms.

Characterization of Polyclonal Antibodies (Pabs)

Sera was collected from rabbits immunized against AP and tested by the various immunoassay procedures. Using a rapid dot blot screening procedure, it was observed that antiserum Scarlet-1 prepared to the unconjugated polypeptide was reactive at the 0.01 $\mu g$ level and produced staining above background with 0.001 $\mu g$ of antigen. At this antigen level, the reaction product from pre-immune serum was barely observable. Scarlet-1 was more potent than serum from a rabbit immunized with the KLH-linked derivative of AP.

Scarlet-1 was characterized with respect to the state of aggregation of AP. Although the dot blot assay may have contained primarily aggregated complexes of the polypeptide, this possibility was examined further by PAGE. AP was electrophoresed in a gel containing 2% SDS under conditions that allowed aggregates to form. An electroblot was prepared from the same gel and immunostained with Scarlet-1. The antiserum detected the lower molecular weight form as well as aggregated species. Thus, antiserum produced in response to the amyloid polypeptide was extremely potent irrespective of the state of aggregation of AP.

Characterization of Monoclonal Antibodies (Mabs)

The supernatants of 24 hybridomas were positive for AP as indicated by the dot blot assay. Of these, three Mabs with particularly strong binding properties were further characterized. Dot blots demonstrated that the three Mabs, designated 4E12, 5E2 and 10H3, were at least as reactive as the polyclonal antisera. In some immunocytochemical experiments (see below), a mixture of the three Mabs in equal parts was used since the mixed preparation was also intensively reactive towards the synthetic peptide. As with polyclonal sera, each of the Mabs reacted strongly with the AP that had been previously treated with SDS prior to electrophoresis.

Immunodetection of Amyloid with Polyclonal Antisera

Initial immunostaining studies employed polyclonal antisera to AP; the data obtained served as a basis for comparison with later experiments using Mabs. Prefrontal cortex (PC) of an AD case contained numerous plaques and interneuronal NFTs that were readily visualized by staining with Thioflavin S (Kelenyi, 1967). Immunostaining the same tissues with Scarlet-1 clearly revealed amyloid plaques that were typical of those seen in the PC and hippocampus of four AD cases.

The same results were obtained with antiserum prepared against the synthetic amyloid polypeptide that had been linked to KLH prior to immunization. The preimmune serum of Scarlet-1 failed to stain AD brain tissue, and the immune serum was infrequently able to detect neuritic plaques in normal controls.

Scarlet-1 antisera strongly bound to the vasculature of AD brains. A longitudinal section of a vessel, stained with Thioflavin S and with immune serum, demonstrated that anti-AP serum detected the most intensely stained features observable with the fluorescent dye. Immunostaining further revealed the close association of amyloid material in the parenchyma with the vascular amyloid. The double label technique applied to blood vessels cut in cross-section confirmed that all vascular layers that bound Thioflavin S were detectable with Scarlet-1 immune serum.

Monoclonal antibodies were prepared to the A4 28 amino acid polypeptide derived from AD brain amyloid (Masters et al., 1985a, FIG. 1). The supernatants of 24 hybridomas were positive; of these, three Mabs with particularly strong binding properties were further characterized. Dot blots demonstrated that the three Mabs, designated 4E12, 5E2 and 10H3, were strongly reactive towards the polypeptide even at extremely high dilutions. In some immunocytochemical experiments (see below) a mixture of the three Mabs in equal parts was used.

Initial studies were aimed at establishing the specificity of the Mabs by immunostaining AD brain sections using an avidin-biotin horseradish peroxidase procedure and analyzing the epitopic distribution by conventional imaging methods. Sections of prefrontal cortex were used. A section stained with thioflavin S, which is known to react with brain amyloid, was counterstained with Mab 5E2. The antibody bound to the amyloid deposit with a distribution that overlapped the fluorescent dye. In other studies, observations on numerous plaques stained with the three Mabs indicated that these antibodies provided more detailed architectonic information than previously reported for AD brain amyloid deposits. The Mabs demonstrated that target epitopes occurred in deposits of different sizes and different morphologies. For example, it was observed that the 10H3 epitope was localized both within a core and in a peripheral ring whereas in other instances the same epitope was more randomly distributed. Immunodetection of an amyloid core surrounded by a ring during the course of these studies was an original finding as were other morphologies described below.

Although it is not known whether or not the three Mabs under consideration are specific for the same or different epitopic sites of the A4 28-mer amyloid polypeptide sequence, when mixed together they provided particularly intense staining of tissues; however, the dark reaction product remained in sharp contrast to low background staining. In control studies, there was no staining with the Mab mixture applied to neurologically normal controls beyond light background staining. The specific and intense staining of amyloid with the mixed Mabs appeared to be the method of choice for more detailed studies using computer-enhanced imaging methods in order to analyze the epitopic distribution without interference from other components of the senile plaque.

As expected, the Mabs that reacted with parenchymal deposits of amyloid also detected the amyloid of blood vessels, as indicated by double staining experiments (thioflavin and Mabs).

In order to improve the visualization of immunostained patterns and gather more detailed information on the distribution of epitopes in the various amyloid conformations, we used computer-enhanced imaging procedures that provided increased resolution of structural features. Sections of prefrontal cortex immunostained with the Mab mixture were viewed by means of a light microscope equipped with a televideo camera that interfaced with a computer for the production of processed images. The images were digitized, size estimates were made, and pseudocolor gray scaling was used to display different levels of density. The major types of amyloid deposits were distinguished in terms of size, internal organization, and internal density.

Four classes of amyloid deposits of different sizes were identified. Small punctate amyloid deposits ($9.06 \pm 0.24$ $\mu$m diameter) were the most commonly observed immunostained configuration. Often seen adjacent to punctate deposits were minute amounts of material that may represent precursor forms. Amyloid accumulations referred to as macular amyloid deposits ($30.87 \pm 1.28$ $\mu$m diameter) were considered together as a class since they are distinguished by a larger diameter. In one example, multiple foci of dense deposits were present throughout the field; a second macular structure of similar size contained only diffuse reaction product. Another example appeared as a darker staining accumulation of amyloid.

Also observed with ring-like amyloid deposits ($40.51 \pm 4.65$ $\mu$m diameter) in which the central region contained little or no immunodetectable amyloid. The rarest configuration was a ring+core amyloid deposit (a ring of amyloid that contained a distinct and separate amyloid core, the ring measured $48.73 \pm 7.36$ $\mu$m diameter and the core measured $12.85 \pm 2.20$ $\mu$m diameter). Previous immunostaining of amyloid deposits with polyclonal sera to a synthetic polypeptide did not detect the ring or ring with core patterns (Master et al., 1985b; Wong et al., 1985).

With respect to neocortex, punctate deposits were predominantly located in layer I and their frequency of occurrence was inversely related to their depth within the cortical mantle. By contrast, macular deposits had a different distribution. When compared with punctate deposits, the macular types were represented to a lesser extent in layer I, but to a greater degree in layers II through VI. Ring shapes occurred in all layers. Ring with core structures were less frequently encountered than the other morphologies. This laminar distribution of the different amyloid classes has not been previously described.

The immunoperoxidase-stained amyloid was subjected to pattern analysis by computer-enhanced imaging methods that allowed visualization of the various epitopic sites according to their density distribution. Using this approach, we observed a greater degree of heterogeneity than was previously appreciated for amyloid in the AD brain. Punctate deposits, in spite of their small diameter, nevertheless exhibited internal gradients of reaction product density. All morphologic types showed a similar gradient of amyloid immunoreactivity. These gradients of reaction product were not attributable to diffusion during the peroxidase step since both short (3-4 min.) and long (7-8 min.) incubations showed deposits of similar size and internal heterogeneity. Irrespective of the overall morphologic variations among the four groups of amyloid deposits, a common feature was the presence of multiple foci of high density.

It is to be emphasized that the Mabs used in the present study exhibited high specificity for amyloid and not necessarily for the senile plaque detectable by silver staining methods. Due to this immunologic specificity, observations were not made with regard to senile plaques per se, which include a variety of cellular and subcellular elements in addition to amyloid (Wisniewski and Terry, 1973); instead, our attention was focused upon morphologic entities identifiable by Mabs with high specificity towards amyloid. In other studies, we have observed that Bielchowsky staining demonstrates that layers II and III contain the greatest number of senile plaques while not revealing the punctate lesions of layer I or other layers in similar tissue sections. For this reason, it is important to emphasize that there is only partial overlap between the immunodectectable amyloid deposit and the classically defined senile plaque.

While the macular amyloid deposits may correspond to the classical descriptions of amyloid within senile plaques (Wisniewski and Terry, 1973), the remaining forms we described appear to be unique. Specifically, Mabs to the A4 28-mer polypeptide visualized a series of amyloid deposits in the AD brain that do not appear to have been previously described: punctate, ring and ring+core amyloid deposits that each have internal density gradients are original findings. The unique aspect of these Mabs suggests their use as powerful reagents for the detaeild investigation of subtypes of AD; such reagents have not been previously available.

The techniques discussed above appear well-suited to the production of Mabs that are unique and which provide new tools to examine the molecular pathogenesis of AD. Therefore, we have used the same methods to generate two additional peptides for the preparation of antibodies. Kang et al. (1987) have reported an A4 amyloid cDNA precursor derived from fetal brain. The sequence predicts two polypeptide regions that appear to be unique to this molecule. The uniqueness was determined after searches by means of the Bionet data bases. The two peptides are as follows:

I. Ala-Glu-Glu-Pro-Tyr-Glu-Glu-Ala-Thr-Glu-Arg-Thr-Thr-Ser-Ile-Ala-Thr-Thr-Thr

II. Arg-His-Val-Phe-Asn-Met-Leu-Lys-Lys-Tyr-Val-Arg-Ala-Glu-Gln-Lys-Asp

The peptides were synthesized and purified. Injection into mice and rabbits produces polyclonal and monoclonal antibodies using procedures previously applied to the A4 peptide.

REFERENCES

Allsop, D., et al., Brain Res. 259:348-352 (1983).
Brown, B. A., et al., J. Neurochem. 40:299-308 (1983).
Brown, B. A., et al., J. Neurochem. 36:143-153 (1981).
Brown, B. A., J. Cell Biol. 94:159-164 (1982).
Divry, P., J. Neurol. Psychiat. 27:643-657 (1927).
Galfre, G., et al., Nature 266:550-552 (1977).
Glenner, G. G., N. Engl. J. Med. 302:1333-1343 (1980).
Glenner, G. G., et al., Biochem. Biophys. Res. Commun. 120:885-890 (1984a).
Glenner, G. G., et al., Biochem. Biophys. Res. Commun. 122:1131-1135 (1984b).
Kang, J., et al., Nature 325:733-736 (1987).
Kelenyi, G., Acta Neuropath. 7:336-348 (1967).
Marotta, C. A., et al., Prog. Brain Res., in press (1986).
Masters, C. L., et al., Proc. Natl. Acad. Sci. U.S.A. 82:4245-4249 (1985a).
Masters, C. L., et al., EMBO J 4:2757-2763 (1985b)
Merrifield, R. B., J. Am. Chem. Soc. 85:2149-2154 (1963).
Merz, P. A., et al., Acta Neuropathol. (Berl.) 60:113-124 (1983).
Wisniewski, H. M., et al., Ann. N.Y. Acad. Sci. 396:119-129 (1982).
Wisniewski, H. M., et al., "Reexamination of the pathogenesis of the senile plaque," in H. M. Zimmerman (ed.), Progress in Neuropathology, pp. 1-26, Grune and Stratton, New York (1973).
Wong, W. C., Et al., Proc. Natl. Acad. Sci. U.S.A. 82:8729-8732 (1985).

Having now fully described this invention, it will be readily apparent that the same can be performed within a wide and equivalent range of parameters, conditions and the like, without affecting the spirit or scope of the invention or any embodiment thereof.

What is new and intended to be covered by Letters Patent of the United States is:

1. Hybridoma cell line ATCC HB9542.
2. An antibody expressed from the hybridoma cell line 10H3 which is deposited at the ATCC under accession no. HB9542.
3. The antibody of claim 2 in detectably labeled form.
4. The antibody of claim 3, wherein said detectable label is selected from the group consisting of a radiolabel, an enzyme label, a cofactor label, a chemiluminescent label, a bioluminescent label, a fluorescent label, a paramagnetic label, and a metal label.
5. The antibody of claim 2 which is bound to a solid carrier.
6. An improved immunoassay for detecting amyloid in brain tissue which comprises contacting said tissue with an antibody to A4-amyloid, under time and conditions sufficient for the binding of the antibody to amyloid in the tissue, and determining whether an immune complex is formed between said antibody and said amyloid, the improvement which comprises utilizing the antibody of claim 2 as said antibody.
7. A method for detecting amyloid in brain tissue which comprises:
    contacting said tissue with an imaging-effective amount of a detectably labeled antibody of claim 3 under time and conditions sufficient for the binding of the antibody to the amyloid in the tissue; and
    detecting said label, thereby establishing the presence of said amyloid in said tissue sample.
8. The method of claim 7, wherein said tissue sample is a tissue section.
9. The method of claim 8 wherein said detection is carried out by imaging in vivo.

* * * * *